United States Patent [19]

Kawaguchi et al.

[11] Patent Number: 4,794,128

[45] Date of Patent: Dec. 27, 1988

[54] POROUS FILM

[75] Inventors: Heihachiro Kawaguchi, Wakayama; Hidenori Shirai, Utsunomiya; Akio Kimura, Wakayama, all of Japan

[73] Assignee: Kao Corporation, Tokyo, Japan

[21] Appl. No.: 54,856

[22] Filed: May 27, 1987

[30] Foreign Application Priority Data

May 28, 1986 [JP] Japan .................................. 61-122999

[51] Int. Cl.$^4$ ........................ C08L 67/00; C08L 77/00
[52] U.S. Cl. ........................................ 521/138; 264/41;
264/45.3; 264/288.8; 264/290.2; 521/143;
521/182
[58] Field of Search ...................... 521/138, 143, 182;
264/41, 45.3, 288.8, 290.2

[56] References Cited

U.S. PATENT DOCUMENTS

| | | | |
|---|---|---|---|
| 3,459,736 | 8/1969 | Dalibor | 536/119 |
| 4,100,238 | 7/1978 | Shinomura | 521/61 |
| 4,105,737 | 8/1978 | Suzuki | 264/154 |
| 4,116,892 | 9/1978 | Schwarz | 521/62 |
| 4,454,256 | 6/1984 | Pellicelli | 521/138 |
| 4,563,317 | 1/1986 | Kamei et al. | 264/83 |
| 4,705,812 | 11/1987 | Ito et al. | 521/92 |
| 4,705,813 | 11/1987 | Ito et al. | 521/92 |

FOREIGN PATENT DOCUMENTS 1044502 10/1966 United Kingdom .

OTHER PUBLICATIONS

Chemical Abstracts, vol. 101, No. 56083a, p. 39 (1984).
Chemical Abstracts, vol. 104, No. 150457j, p. 72 (1986).

*Primary Examiner*—Morton Foelak
*Attorney, Agent, or Firm*—Birch, Stewart, Kolasch & Birch

[57] ABSTRACT

A porous film comprises a polyolefin resin, a filler and a polyester obtained from a polybasic acid, a polyhydric alcohol and a monobasic acid having 14 to 22 carbon atoms and/or a monohydric alcohol having 12 to 22 carbon atoms or a polyester obtained from a polybasic acid and a monohydric alcohol, the film being obtained by melting and moulding and then stretching. It has a good permeability to moisture and impermeability to liquid, and is useful for a sanitary napkin.

9 Claims, No Drawings

POROUS FILM

Field of the Invention

This invention relates to a porous film. The purpose of the invention is to provide a porous film which is required to have flexible hand feeling, good moisture permeable anti-leakage, and strength together in the field of sanitary materials, medical materials, and clothing material. More specifically, the purpose of the invention is to provide a porous film which is suitable as a component for the fastening function in cooperation with a fastening tape, such as a moisture permeable anti-leakable film for disposable diapers, and which has the above-mentioned properties.

Description of the Prior Art

Many attempts for obtaining porous films by kneading polyolefine resin with filler, melt-forming into film, and stretching the film uniaxially or biaxially have been made heretofore.

These conventional porous films, in the case of uniaxial stretching, are disadvantageously anisotropic in strength, that is, the tear strength in the stretching direction and the tensile strength in the transverse direction are very low. In order to improve the anisotropy in strength, a method in which film is stretched at a ratio as low as possible has been proposed. However, it is difficult to obtain uniform stretched film by such method.

The problem of anisotropy is resolved by applying biaxial stretching. This method, however causes the disadvantage of remarkably decreased stretchability.

On the other hand, mixtures comprising only polyolefin resin and filler will not give porous films with flexible hand feeling by stretching. More recently, as the means to resolve these problems compounds which contain liquid hydrocarbon or other additives as a third component in addition to polyolefin resin and filler have been proposed. For instance, liquid polybutadiene, liquid polybutene, and liquid polybutadiene with hydroxyl group on the ends thereof are disclosed as the third component for improving of the above-mentioned problems in Japanese Patent Laid-Open No. 58(1983) - 15538, and liquid polyisoprene rubber in Japanese Patent Laid-Open No. 58 (1983) -149925, respectively.

However, the above-mentioned techniques for improvement can not fully satisfy, the requirements with regard to the balance between moisture permeability and tear strength in the stretched direction (longitudinal tear strength). This is especially the case when the film is used, for instance, as a moisture permeable anti-leakage component member of disposable diapers which serves a fastening function together with a fastening tape. If the longitudinal tear strength is low, the stress is centered locally on the moisture permeable anti-leakage film around the peripheral portion of the fastening tape to cause breakage around the fastening tape when the fastening tape is fastened and unfastened or during use. Thus the usable field is limited extremely.

Summary of the Invention

The inventors of the present invention have made efforts to provide a porous film which resolves the above-mentioned problems. The inventors have found that the longitudinal tear strength of a porous film can be improved by adding particular polyester as a third component, while retaining flexible hand feeling and good moisture permeable anti-leakage to attain this invention.

A porour film of the invention comprises a polyolefin resin, a filler and a polyester obtained from a polybasic acid, a polyhydric alcohol and a monobasic acid having 14 to 22 carbon atoms and/or a monohydric alcohol having 12 to 22 carbon atoms or a polyester obtained from a polybasic acid and a monohydric alcohol, the film being obtained by melting and moulding and then stretching.

The film of the invention comprises the above defined polyester, including three preferable embodiments, a polyester obtained from a polybasic acid and a monohydric alcohol, a polyester obtained from a poyhydric alcohol, a polybasic acid and a monohydric alcohol having 12 to 22 carbon atoms and a polyester obtained from a polyhydric alcohol, a polybasic acid and a monobasic acid having 14 to 22 carbon atoms.

It is preferable that a dibasic acid such as adipic acid, succinic acid, a derivative of succinic acid and a dimeric acid is used as the polybasic acid. The monohydric alcohol used to form a polyester with a polybasic acid is preferred to have 12 to 22 carbon atoms. A monomer mixture of the same kind may be used for the polyester.

The invention has a good permeability to moisture and is impermeable to liquid. Thus, the invention is useful for a sanitary napkin.

Detailed Description of the Invention

The present invention will be described in detail hereinbelow.

Polyolefin resins used in the present invention refer to polymers which contain principally mono-olefin homopolymers and copolymers of ethylene, propylene, and butene. Representative examples include high density polyethylene, low density polyethylene, linear low density polyethylene, polypropylene, ethylene-propylene copolymer, polybutene, ethylene-vinyl acetate copolymer, and mixtures thereof. Among these materials linear low density polyethylene is especially suitable because of the flexibility and toughness thereof.

In the present invention, inorganic fillers such as calcium carbonate, gypsum, talc, clay, kaolin, silica, diatomaceous earth, magnesium carbonate, barium carbonate, magnesium sulfate, barium sulfate, calcium phosphate, aluminium hydroxide, zinc oxide, titanium oxide, alumina, mica, zeolite, and carbon black, and organic fillers such as powders of wood and pulp are used as the filler. These fillers may be used separately or in admixture.

Fillers having a mean particle diameter of $30\mu$ or less are preferably used, and more preferably fillers of $10\mu$ or less, and especially 0.5 to $5.0\mu$ are used.

The surface treatment of filler is important for the homogeneous distribution of the filler in resins. Surface treatment agents which make the surface hydrophobic such as fatty acids or metal salts thereof are preferably used.

Polyesters used in the present invention refer to polyesters of polybasic acid, polyhydric alcohol, monobasic acid with 14 to 22 carbon atoms, and/or monohydric alcohol with 12 to 22 carbon atoms. The combination of these acids and alcohols are selected from the view point of the balance of affinity of the polyesters for polyolefin and filler considering the number of ester groups in an unit weight of polyester and the degree of branching of hydrocarbon chain. Polybasic acid, polyhydric alcohol, monohydric alcohol, and monobasic acid which constitute polyesters involved in the invention will be described hereinbelow.

Monobasic acid used in the present invention includes monocarboxylic acids having 14 or more carbon atoms, polybasic acids include dicarboxylic acids, tricarboxylic acids, and tetracarboxylic acids, monohydric alcohol includes monohydric alcohols having 12 or more carbon atoms, and polyhydric alcohol includes diols, trimethylol propane, pentaerithritol, dipentaerithritol, sorbitol, and sucrose.

If the number of carbon atoms of monobasic acid is 12 or less or the number of carbon atoms of monohydric alcohol is 10 or less, probably because the balance in affinity of the polyester for filler and polyolefin deviates from the acceptable condition, various disadvantages are caused. For example, the third component is locally deposited during film formation, the film is unevenly stretched, or the longitudinal tear strength is reduced.

Polyesters involved in the present invention may be polyesters which are obtained by dehydration condensation of these polybasic acids and polyhydric alcohols. Such end group-esterified polyesters are preferable that, in the case of a carboxylic end group, most of the end groups are esterified with monohydric alcohol having a long hydrocarbon chain such as stearyl alcohol, oleyl alcohol, and Guerbet alcohol. In the case of an alcoholic end group, most of the end groups are esterified with monobasic carboxylic acid having a long hydrocarbon chain such as stearic acid, hydroxy-stearic acid, oleic acid, and isostearic acid, but all end groups are not necessarily esterified. Acids and alcohols having a branched chain are more preferably used.

Specific examples of preferable polyester include polyesters of diethyleneglycol and dimeric acid wherein both carboxylic end groups or alcoholic end groups of which polyesters are esterified entirely or partially with stearyl alcohol or stearic acid; polyesters of 1,3- butanediol and adipic acid wherein both end groups of which are esterified with hydroxy stearic acid, hexa-ester comprising trimethylol propane, adipic acid, and stearic acid, octa-ester comprising penta-erithritol, adipic acid, and stearic acid, dodeca-ester comprising dipentaerithritol, adipic acid, and stearic acid; polyesters utilizing dimeric acid or hydrogenated dimeric acid instead of adipic acid which is the constituent of the above-mentioned polyesters; and polyesters utilizing isostearic acid instead of stearic acid.

The preferable proportion of polyolefin resin, filler, and the third component utilized in the present invention is in the range from 50 to 250 parts by weight of the filler and 5 to 50 parts by weight of the third component based on 100 parts by weight of polyolefin resin.

Polyolefin resin, filler, and the third component may be mixed according to conventional processes. For instance, materials are preliminarily mixed in a Henschel mixer or in a super mixer, and kneaded in a twin-screw extruder.

Film may be formed using conventional processes such as tubular film process and T-die process, and so on. Though conventional orientation methods such as uniaxial rolling, successive and simultaneous biaxial stretching may be applied, uniaxial stretching with a ratio of 1.5 to 3.0 is especially preferable.

The porous film of the invention is unexpectedly improved in respect to tear strength, with particular against a tearing force applied at the vertical direction of the stretching, that is, strength to longitudinal tearing. A test about the longitudinal tear strength was carried out by applying to a test film a tearing force at the vertical direction of the stretching direction.

EXAMPLES

The invention will be described in detail referring to examples hereinafter, however the scope of the invention is by no means limited to the examples.

The composition and property of polyesters used in the examples are listed in Table 1. These polyesters were obtained through a usual dehydration esterification reaction.

EXAMPLE 1

100 parts by weight of linear polyethylene resin (Ultozex)

TABLE 1

| Polyester No. | Composition of ester (charged theoretical molar ratio) | SV | AV | OHV | Total theoretical carbon number |
|---|---|---|---|---|---|
| E1 | S-40/TMP/DA = 4/2/1 | 240 | 1.5 | 9.9 | 90 |
| E2 | DA/DEG/K-86 = 2/1/2 | 130 | 5.0 | 13 | 112 |
| E3 | DA/DEG/GA = 2/1/2 | 125 | 3.8 | 12 | 116 | note
SV: saponification value
AV: acid value
OHV: hydroxyl value
GA: $C_{20}$ Guerbet alcohol
TMP: trimethylol propane
AA: adipic acid
DA: dimeric acid (Emery Corp. Empol 1010)
S-40: stearic acid (Kao Corporation Lunak S-40)
K-86: stearyl alcohol (Kao Corporation Kalcohl 86)
DEG: diethylene glycol 3021F, Mitsui Petrochemical Industries, Ltd.), 150 parts by weight of surface treated calcium carbonate (mean particle diameter of 1μ), and 30 parts by weight of polyester E1 as the third component were preliminarily mixed in a super mixer of 20l (Kawada Works Ltd.), and the obtained mixture was kneaded and pelletized using a twin-screw kneader PCM-45 (Ikegai Corporation).

The pellets were fed to an extruder having a screw diameter of 50 mm and extruded through a T-die to form a film having a thickness of 70μ. The obtained film was extended uniaxially using a roll type uniaxially extending machine.

Operation conditions are shown hereinunder.
Width of film=400 mm,
Preheating temperature=80° C.,
Extention temperature=50° C.,
Extention ratio=2.2,
Winding speed=22 m/min.

Properties of the obtained porous film are shown in Table 2.

Test procedures for each property are shown hereinunder.
Moisture permeability:according to JIS Z-0208.
Longitudinal tear strength:according to JIS P-8116.

EXAMPLES 2 AND 3

Porous films were prepared in the same manner as described in Example 1 except that the third component was changed as shown in Table 2.

The evaluation results of the properties of each film are shown in Table 2.

REFERENCE EXAMPLES 1 TO 4

Porous films were obtained in the same manner as described in Example 1 except that hydrocarbons shown in Table 2 were used as the third component instead of polyester.

The evaluation results of the properties of each film are shown in Table 2.

TABLE 2

| | Third component | Proportion parts by weight*1 | moisture permeability*2 | longitudinal tear strength*3 |
|---|---|---|---|---|
| Example | | | | |
| 1 | Polyester E1 | 30 | 1.81 | 68 |
| 2 | Polyester E2 | 30 | 1.75 | 66 |
| 3 | Polyester E3 | 30 | 1.77 | 69 |
| Reference example | | | | |
| 1 | Liquid isoprene LIR-30*4 | 30 | 1.79 | 17 |
| 2 | Hydrogenated polyisoprene LIR-290*5 | 30 | 1.29 | 16 |
| 3 | Polybutene HV-100*6 | 30 | 0.69 | 51 |
| 4 | Lucant 600*7 | 30 | 0.53 | 62 | note:
*1 proportion in parts by weight based on 100 parts by weight of polyolefin resin.
*2 g/100 cm$^2$ Hr.
*3 g/50µ thickness.
*4 Kuraray Isoprene Chemical Co., Ltd. Kuraprene LIR-30.
*5 Kuraray Isoprene Chemical Co., Ltd. Kuraprene LIR-290.
*6 Idemitsu Petrochemical Industries Ltd. polybutene HV-100.
*7 Mitsui Petrochemical Industries Ltd. ethylene-α-olefin oligomer.

EXAMPLE 4, 5 AND 6

Porous films were prepared in the same way as shown in Example 1 by using the polyesters listed in Table 3, and by examining them with respect to their properties. Results are shown in Table 4.

TABLE 3

| Polyester No. | Composition of ester (charged theoretical molar ratio) | SV | AV | OHV | Total theoretical carbon number |
|---|---|---|---|---|---|
| E4 | GA/AA = 2/1 | 147 | 0.4 | 6.0 | 46 |
| E5 | GA/ASA = 2/1 | 118 | 2.8 | 6.2 | 61 |
| E6 | GA/K-86/AA = 1/1/1 | 159 | 0.1 | 6.8 | 43 | note:
GA: C$_{20}$ Guerbet alcohol.
AA: adipic acid.
ASA: C$_{21}$ alkenyl succinic acid.
K-86: stearyl alcohol (Kao Corporation, Kalcohol 86).

TABLE 4

| Example | Third component | Proportion parts by weight | moisture permeability | longitudinal tear strength |
|---|---|---|---|---|
| 4 | Polyester E4 | 30 | 1.54 | 91 |
| 5 | Polyester E5 | 30 | 1.53 | 89 |
| 6 | Polyester E6 | 30 | 1.65 | 73 |

The moisture permeability of 1.0 g/100 cm$^2$ Hr or more determined according to JIS Z-0208 is demonstrated to be effective for prevention of stuffiness during use when the film is used as moisture permeable anti-leakage sheet for sanitary material of disposable diapers. As shown in Table 2, Reference examples 1 and 2 lie in the acceptable range of moisture permeability, but their tear strength is extremely low. Therefore, therefore the films are unusable in the field where film serves as a member for fastening function with fastening tape together. Reference examples 3 and 4 lie in the acceptable range of longitudinal tear strength, but their moisture permeability is very low. Therefore the effect in prevention of stuffiness can not be expected during use.

On the other hand, in Examples 1 to 6 of the present invention both, the moisture permeability and the longitudinal tear strength are remarkably improved. That is, the longitudinal tear strength is improved to a higher level of approximately 4 times that of Reference examples 1 and 2 which have the moisture permeability of 1.0 g/100 cm$^2$ Hr or more. Moreover, and in comparison with Reference examples 3 and 4, the longitudinal tear strength is increased by a level of 10 to 20% and the moisture permeability is increased to a higher level of 2.5 to 3.3 times.

What is claimed is:

1. A porous film which comprises a polyolefin resin, a filler and a polyester obtained from a polybasic acid, a polyhydric alcohol and a monobasic acid having 14 to 22 carbon atoms and/or a monohydric alcohol having 12 to 22 carbon atoms or a polyester obtained from a polybasic acid and a monohydric alcohol, the film being obtained by melting and moulding and then stretching.

2. A porous film as claimed in claim 1, in which said polyester has been obtained from a polybasic acid and a monohydric alcohol.

3. A porous film as claimed in claim 1, in which said polyester has been obtained from a polyhydric alcohol, a polybasic acid and a monohydric alcohol having 12 to 22 carbon atoms.

4. A porous film as claimed in claim 1, in which said polyester has been obtained from a polyhydric alcohol, a polybasic acid and a monobasic acid having 14 to 22 carbon atoms.

5. A porous film as claimed in claim 1, in which one monomer for the polyester is branched.

6. A porous film as claimed in claim 1, which has been uniaxially stretched 1.5 to 3.0 times.

7. A porous film as claimed in claim 1, which comprises 100 parts by weight of the polyolefin resin, 50 to 250 parts by weight of the filler and 5 to 50 parts by weight of the polyester.

8. A porous film as claimed in claim 1, in which said polyolefin resin is polyethylene or polypropylene.

9. A porous film as claimed in claim 1, in which said polyolefin is a linear, low density polyethylene.

* * * * *